(12) United States Patent
Geangu et al.

(10) Patent No.: US 10,973,995 B2
(45) Date of Patent: Apr. 13, 2021

(54) CONTAINER HOLDER WITH A TEMPERATURE CONTROL DEVICE FOR AN INJECTOR

(71) Applicant: ulrich GmbH & Co. KG, Ulm (DE)

(72) Inventors: Anamaria Geangu, Ulm (DE); Markus Götz, Blaustein (DE)

(73) Assignee: Ulrich GmbH & Co. KG, Ulm (DE)

( * ) Notice: Subject to any disclaimer, the term of this patent is extended or adjusted under 35 U.S.C. 154(b) by 393 days.

(21) Appl. No.: 16/159,947

(22) Filed: Oct. 15, 2018

(65) Prior Publication Data

US 2019/0255261 A1    Aug. 22, 2019

(30) Foreign Application Priority Data

Feb. 22, 2018    (DE) ...................... 10 2018 104 002.4

(51) Int. Cl.
*A61M 5/44* (2006.01)
*A61D 7/00* (2006.01)
(Continued)

(52) U.S. Cl.
CPC ................ *A61M 5/44* (2013.01); *A61D 7/00* (2013.01); *A61M 5/007* (2013.01); *A61M 5/142* (2013.01);
(Continued)

(58) Field of Classification Search
CPC ...... A61M 2205/123; A61M 2205/128; A61M 5/007; A61M 5/1409; A61M 5/142;
(Continued)

(56) References Cited

U.S. PATENT DOCUMENTS 4,473,739 A * 9/1984 Scheiwe ................. A23L 3/365
                                                            219/385
4,709,135 A    11/1987 Dietrich et al.
(Continued)

FOREIGN PATENT DOCUMENTS

DE    20 2015 102187 U1    8/2016
EP        1526881 B1    12/2015
(Continued)

OTHER PUBLICATIONS

European Search Report dated Mar. 11, 2019 for Application No. 18 18 5221.

*Primary Examiner* — Quynh-Nhu H. Vu
(74) *Attorney, Agent, or Firm* — Paul D. Bianco; Fleit Intellectual Property Law

(57) ABSTRACT

A container holder for an injector for injecting a fluid into the human or animal body includes at least one container clamping member for clamping onto a container that is filled with the fluid and a temperature control device for bringing the temperature of the container to a predefined temperature. To be able to clamp containers of different shapes and sizes onto the container holder and to bring the temperature of the containers to a desired temperature without any thermal loss, by means of the temperature control device, and to ensure easy and unimpeded clamping and removal of the container, the temperature control device is connected to a transporting device, by means of which the temperature control device can be brought into and out of thermal contact with the container that is clamped onto the container clamping member.

18 Claims, 5 Drawing Sheets

(51) Int. Cl.
  *A61M 5/00*   (2006.01)
  *A61M 5/14*   (2006.01)
  *A61M 5/142*  (2006.01)
  *A61M 5/168*  (2006.01)

(52) U.S. Cl.
  CPC .......... *A61M 5/1409* (2013.01); *A61M 5/445* (2013.01); *A61M 5/16831* (2013.01); *A61M 2205/123* (2013.01); *A61M 2205/128* (2013.01)

(58) Field of Classification Search
  CPC .... A61M 5/16831; A61M 5/44; A61M 5/445; A61M 1/662; A61M 1/664; A61M 1/369; A61M 2205/3368; A61M 2205/3372; A61M 2230/50
  See application file for complete search history.

(56) References Cited

U.S. PATENT DOCUMENTS

| | | | | |
|---|---|---|---|---|
| 5,782,796 | A | * | 7/1998 | Din .................. A61M 1/28 604/27 |
| 5,999,701 | A | * | 12/1999 | Schmidt ............... A61M 5/445 219/535 |
| 2010/0051135 | A1 | * | 3/2010 | Fago ................ A61M 5/14546 141/2 |
| 2010/0059498 | A1 | * | 3/2010 | Hansen ................ A61M 5/445 219/400 |
| 2010/0168671 | A1 | * | 7/2010 | Faries, Jr. ............ A61M 5/148 604/114 |
| 2011/0046551 | A1 | * | 2/2011 | Augustine ............ A61F 7/0085 604/113 |
| 2011/0282281 | A1 | * | 11/2011 | Kammer ............ G05D 23/1931 604/113 |
| 2014/0088494 | A1 | * | 3/2014 | Shearer, Jr. ........... A61M 5/007 604/67 |
| 2014/0207063 | A1 | * | 7/2014 | Hyun ................ A61J 15/0026 604/113 |
| 2016/0317735 | A1 | | 11/2016 | Koch |
| 2016/0354538 | A1 | * | 12/2016 | Neer ................ A61M 5/14546 |

FOREIGN PATENT DOCUMENTS

| | | |
|---|---|---|
| FR | 1384353 A | 1/1965 |
| GB | 1444265 A | 7/1976 |
| WO | 2010/082826 A1 | 7/2010 |
| WO | 2014/098675 A1 | 6/2014 |

\* cited by examiner

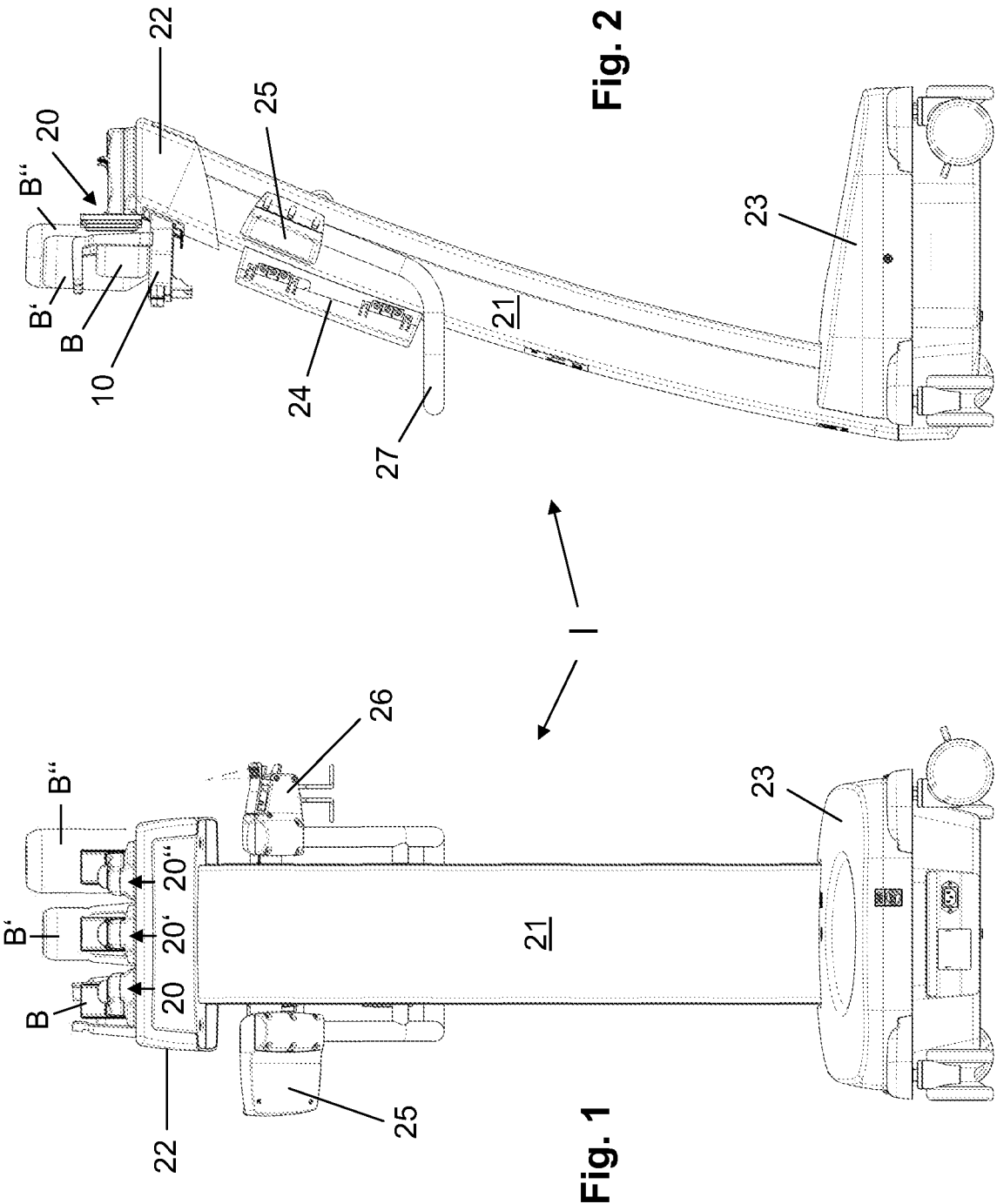

CONTAINER HOLDER WITH A TEMPERATURE CONTROL DEVICE FOR AN INJECTOR

FIELD OF THE DISCLOSURE

The disclosure relates to a container holder for an injector for injecting fluids, for example, contrast media, into the human or animal body.

BACKGROUND

In imaging procedures performed on the human or animal body for the purpose of medical diagnostics and the visualization of structures and functions of the body tissues and organs, such as magnetic resonance imaging (MM) and computed tomography (CT), contrast media are frequently administered into the body before or during the procedure in order to enhance the contrast of the images acquired. By comparing the images acquired during the imaging procedure with and without the administration of contrast media, the reliability of the images acquired can be improved, and it is possible to more accurately identify foci of inflammation or tumors marked, for example, by a more intense white color.

For the intravenous injection of contrast media, injectors are used, which transfer a contrast medium stored in a storage container into a patient's tube by means of a pump which, for the intravenous administration of the contrast medium into the body of a patient, is connected to a cannula. As a rule, a delivery mechanism with a peristaltic pump is used to transfer the contrast medium from the storage container into the patient's tube. To this end, provision is made for a transfer device in the form of a tubular system or a cartridge comprising fluid channels which transfer the contrast medium from the storage container into a pump tube which is inserted into the peristaltic pump and connected to the patient's tube. The peristaltic pump delivers the contrast medium from the storage container into the patient's tube.

This type of injector for the administration of contrast media for use in X-ray and nuclear spin resonance tomography is known, for example, from DE 20 2015 102 187 U1. This injector comprises a plurality of storage containers, which are filled with a fluid to be injected (for example, a contrast medium or a rinsing solution), and a cartridge which is replaceably disposed on the injector and which is connected to a pump tube and, via connecting tubes, to the storage containers. The cartridge comprises a body with fluid channels formed therein, which are connected via the connecting tubes to the storage containers and to the pump tube. To deliver the fluid to be injected (contrast medium or rinsing solution, for example, NaCl) from the storage containers through the fluid channels of the cartridge and through the pump tube connected thereto into the patient's tube, a peristaltic pump (a roller pump) is provided, which periodically squeezes the pump tube against a counter surface and thereby delivers the fluid contained in the pump tube into the patient's tube.

To avoid hypothermia, trauma or other health impairments, fluids that are to be administered, for example, by infusion or intravenous injection, into the human or animal body should be at least approximately close to the body temperature. To bring the fluid to be injected to body temperature, and to maintain it thereat, the, it is known from the prior art to use injectors with heating devices, by means of which the fluid can be heated to the body temperature and maintained at this temperature during the injection procedure. Thus, for example, EP 1 526 881 B1 discloses an injector for injecting fluids from a syringe into an animal subject, which injector comprises a heatable syringe clamping member for clamping the syringe that is filled with the fluid. A different heating device comprising a heatable fluid tube for heating fluids contained therein and intended for administration into the body of a patient has been disclosed in WO 2014/098675 A1.

The heating devices integrated into injectors for heating or cooling fluids to be injected at body temperature, such as the heatable syringe clamping member known, e.g., from EP 1 526 881 B1, have a disadvantage in that they are shaped to fit the shape and size of the container containing the fluid. Consequently, only containers with a predefined shape and size can be used with the heating device and be heated to and maintained at body temperature. However, fluids to be injected, such as contrast media and rinsing solutions, as a rule, are bottled in storage containers of different shapes and sizes. It is therefore not possible to simply attach different storage containers to a clamping member on the injector, which clamping member is intended for a specific and complementarily shaped container, and to heat it to body temperature and maintain it thereat.

Therefore, there is a need for an injector with a container holder which is suitable for clamping onto containers of different shapes and sizes and which comprises a temperature controlling device, by means of which different containers that are clamped onto the clamping member can be heated and, in particular, maintained at body temperature. At the same time, it should be possible to control the temperature as energy-efficiently as possible without any thermal loss, and access to the container for clamping and removing the container should be easy and unimpeded.

SUMMARY

Accordingly, one aspect of the disclosure relates to a container holder for an injector that addresses at least some of these needs. Preferred embodiments of the container holder are also disclosed. In addition, methods of controlling the temperature of a container which is filled with an injection fluid and which is clamped onto the container clamping member of an injector are also disclosed.

In one embodiment, the container holder according to the disclosure comprises at least one container clamping member for clamping onto a container filled with the fluid and a temperature control device for heating or cooling the container to a predefined temperature, in particular to the body temperature of a patient, into whose body the fluid is to be injected. According to the disclosure, the temperature control device is connected to a transporting device that is clamped onto the container clamping member, by means of which the temperature control device can be moved into and out of contact with the container.

The container clamping member is designed to allow a variety of containers of different shapes and sizes to be clamped onto the at least one container clamping member. After a container has been clamped onto the container clamping member, the transporting device can be used to move the temperature control device to the container so as to bring the temperature control device, irrespective of the shape and size of the container, into thermal contact with the outside surface of the container. After the container has been emptied, the temperature control device can be moved away from the clamped-on container by means of the transporting device so that the temperature control device is located at a distance from the container. In this manner, a simple removal of the emptied container from the container clamping member and an unimpeded clamping on of a new container filled with an injection fluid is made possible.

By means of the transporting device, the temperature control device can preferably be moved at least between one rearward position and at least one forward position, with the temperature control device being located at a distance from the container that is clamped onto the container clamping member, when in the rearward position, and in in thermal contact with the container when in the forward position. To be able to secure the transporting device in the rearward position and/or in the forward position, a locking mechanism is preferably provided. To allow an easy and unimpeded clamping and removal of a container onto and from the container clamping member, it is recommended that the transporting device be secured in the rearward position. To ensure and maintain good thermal contact between the temperature control device and the container during the injection procedure, it is recommended that the transporting device be secured in the forward position.

Since different containers of different shapes (for example, bottles, cans or bags) and sizes (for example, having liquid volumes from 100 mL to 1000 mL) are to be clamped onto the container clamping member, it is advantageous if the locking mechanism, in addition to the rearward position, comprises a plurality of forward locking positions, with the forward locking positions preferably being selected so that the temperature control device is in thermal contact, for example, with a container of a predefined standard size and shape (for example, a 500 mL or a 1000 mL bottle) when such a container is clamped onto the container clamping member. The locking mechanism can secure the transporting device in the rearward position and/or in one of the forward locking positions. However, it is also possible to clamp containers of a non-standardized size or shape onto the container clamping member.

For easy manual disengagement of the locking mechanism from the rearward position, it is useful to provide a manually operable push button which, when activated, unlocks the transporting device in the rearward position and thereby enables a movement of the temperature control device into a forward position in which the temperature control device is in thermal contact with a container that is clamped onto the container clamping member.

According to a practical example of the disclosure, the transporting device comprises a spring, and the temperature control device is moved by the elastic force of the spring in the direction of a container that is clamped onto the container clamping member so as to bring the temperature control device into thermal contact with the container. To this end, the transporting device can comprise a housing which can be secured to the injector and a carriage which can move relative to the housing and on which the temperature control device is disposed so as to be linearly movable. The carriage is preferably movably mounted on a guide member in or on the housing and is able to move along the guide member against the elastic force of the spring. This enables the carriage with the temperature control device attached thereto to be automatically pushed by the spring in the direction of the container clamping member when the locking mechanism is disengaged from the rearward position (by activating the push button). As a result, the temperature control device is automatically transported by the transporting device into a forward position to a container that is located in the container clamping member until the temperature control device is in (thermal) contact with the container. To ensure that the movement of the temperature control device automatically triggered by the spring does not take place too abruptly or too rapidly, the movement of the carriage is preferably damped by a damping element. This can be implemented, for example, by a gear rack which is disposed on the carriage and which is connected to a damping element designed in the form of a rotational damper and attached to the housing of the transporting device. It is, however, also possible to attach the damping element to the carriage and the gear rack to the housing. The damping element can also be designed as a piston damper.

In the embodiment of the disclosure in which the transporting device comprises a spring and the temperature control device is moved by the elastic force of the spring in the direction of a container that is clamped onto the container clamping member so as to bring the temperature control device into thermal contact with the container, it is not absolutely necessary for the locking mechanism, in addition to the rearward locking position, to provide yet one other or a plurality of forward locking positions since the spring already pushes the temperature control device against the outside surface of the container and thereby makes thermal contact with the container and maintains this contact during an injection procedure. Especially in this embodiment of the disclosure, it is possible to clamp even containers of non-standardized sizes or shapes onto the container clamping member.

Once the injection procedure has been completed or an emptied container has been replaced with a new container that is filled with an injection fluid, the temperature control device can be brought out of contact with the container by using the transporting device to move the temperature control device away from the container. To this end, it is useful if a handle part is molded onto the carriage, by means of which handle part the movable carriage can be manually moved against the elastic force of the spring so as to allow the carriage to be moved from a forward position, in which the temperature control device is in thermal contact with the container, back into the rearward position, in which the temperature control device is positioned at a distance from the container. Preferably, the current supply to the temperature control device is automatically cut off when the temperature control device is not in contact with the container. In this manner, heating energy can be saved.

To create the largest possible thermal contact surface between the temperature control device and a container that is clamped onto the container clamping member, it is useful if the temperature control device in the region of a heat transfer zone, which comes into thermal contact with the outside surface of the container, is designed in such a manner that the temperature control device, irrespective of the shape and size of the container, is able to fit as closely as possible to the outside surface of the container. This ensures an efficient heat transfer without any thermal loss.

Since the conventionally used storage containers for contrast media have a cylindrical shape, it is useful if at least the heat transfer zone of the temperature control device facing the container has a curved or, more specifically, a concavely curved cross section. The heat transfer zone of the temperature control device preferably has a part-cylindrical shape, for example, the shape of half of a cylinder, the shape of a third of a cylinder or the shape of a quarter of a cylinder.

To ensure an efficient heat transfer from the heat transfer zone to the container, the heat transfer zone is preferably made of an elastic and heat-conducting material. The elasticity of the heat transfer zone allows the heat transfer zone to fit closely to the shape of the container and thus makes it possible to optimize the heat transfer surface once the temperature control device has been brought into contact with the container by means of the transporting device. To ensure optimum heat transfer, the heat transfer zone is configured as a heat-conducting element made of a heat-conducting material, such as metal, graphite or a thermally conductive plastic material, which sits close to the outside surface of the container. The heat-conducting element can also be configured as a multi-component plastic injection molded part which comprises a main body made of a rigid plastic and an elastic layer made of an elastomer.

The temperature control device preferably comprises an adjustable heating element or cooling element. The heating element used can be an electrical heating element, for example, a current-carrying heating filament or a PTC heating element. Depending on the direction of the current flow, a Peltier element can be used both as a heating element and as a cooling element. The heating or cooling element can heat or cool the container and the fluid contained therein to a predefined target temperature (in particular to temperatures in a range from 28° C. to 37° C.) and/or to maintain the container and the fluid at that temperature during an injection procedure (which can take a few minutes up to several hours). In most cases, the temperature of the containers filled with a fluid to be injected has been pre-adjusted so that the containers are clamped onto the container clamping member at a temperature within the range of the target temperature desired (in particular a body temperature of approximately 37° C.). In that case, the heating or cooling element serves to maintain the adjustable target temperature throughout the injection procedure. Preferably, provision is made for a temperature sensor which measures the temperature of the container and transmits it to a control unit of the injector, with the control unit supplying the temperature control device with the electrical current required for operating the heating element or the cooling element and ensuring that the temperature of the container is maintained at the target temperature set on the control unit.

To avoid energy losses, the control unit preferably cuts off the current supply to the temperature control device when the heat transfer zone of the temperature control device is not in contact with the container. To this end, a sensor is preferably provided for detecting the position of the transporting device, or more specifically the position of the temperature control device moved by means of the transporting device, and the position signal detected by the sensor is transmitted to the control unit so that the control unit can cut off the current supply to the heating or cooling element as soon as the temperature control device (or the transporting device) reaches or leaves a predefined position.

In a preferred practical example of the disclosure, the temperature control device is able to pivot with respect to the transporting device about an axis which is vertical relative to the direction of transport (direction of movement of the carriage). This can be implemented, for example, by a pivotably mounted base member of the temperature control device on a front face of the transporting device, in particular on the front face of the carriage. Because of the ability of the temperature control device to pivot with respect to the transporting device, the temperature control device can tilt with respect to a vertical plane. As a result, it is possible to closely fit the temperature control device even to containers (such as bottles with a bottleneck) which do not have a (perfect) cylindrical outside surface, and tilting movements of the container can be compensated for in the container clamping member.

The cross section of the base member is preferably curved or, more specifically, concavely curved. A thermal insulator can be disposed on the base member and, on top thereof, the cooling or heating element. The thermal insulator ensures that the cooling or heating energy supplied by the cooling or heating element flows only (forwardly) in the direction of the container and not (rearwardly) in the direction of the base member, thereby ensuring an efficient heat transfer to the container, the temperature of which is to be controlled. The thermal insulator is preferably made of an elastically deformable material, such as a foamed material or, more specifically, a foamed plastic. This improves the ability of the temperature control device to fit closely to an outside surface of a container and increases the heat transfer surface. To improve and make the heat transfer more uniform, preferably a heat-conducting element made of a heat-conducting material, such as metal, graphite or a thermally conductive plastic, can be disposed on the cooling or heating element, which heat-conducting element sits close to the outside surface of the container whenever the temperature control device is in thermal contact with a container that is clamped onto the container clamping member.

BRIEF DESCRIPTION OF THE DRAWINGS

These and other advantages and features of the disclosure follow from the practical example described in greater detail below, with reference to the appended drawings. The drawings show:

FIG. 1: a rear view of an injector for injecting a fluid into the human or animal body;

FIG. 2: a lateral view of the injector shown in FIG. 1;

DETAILED DESCRIPTION

Figure 3:
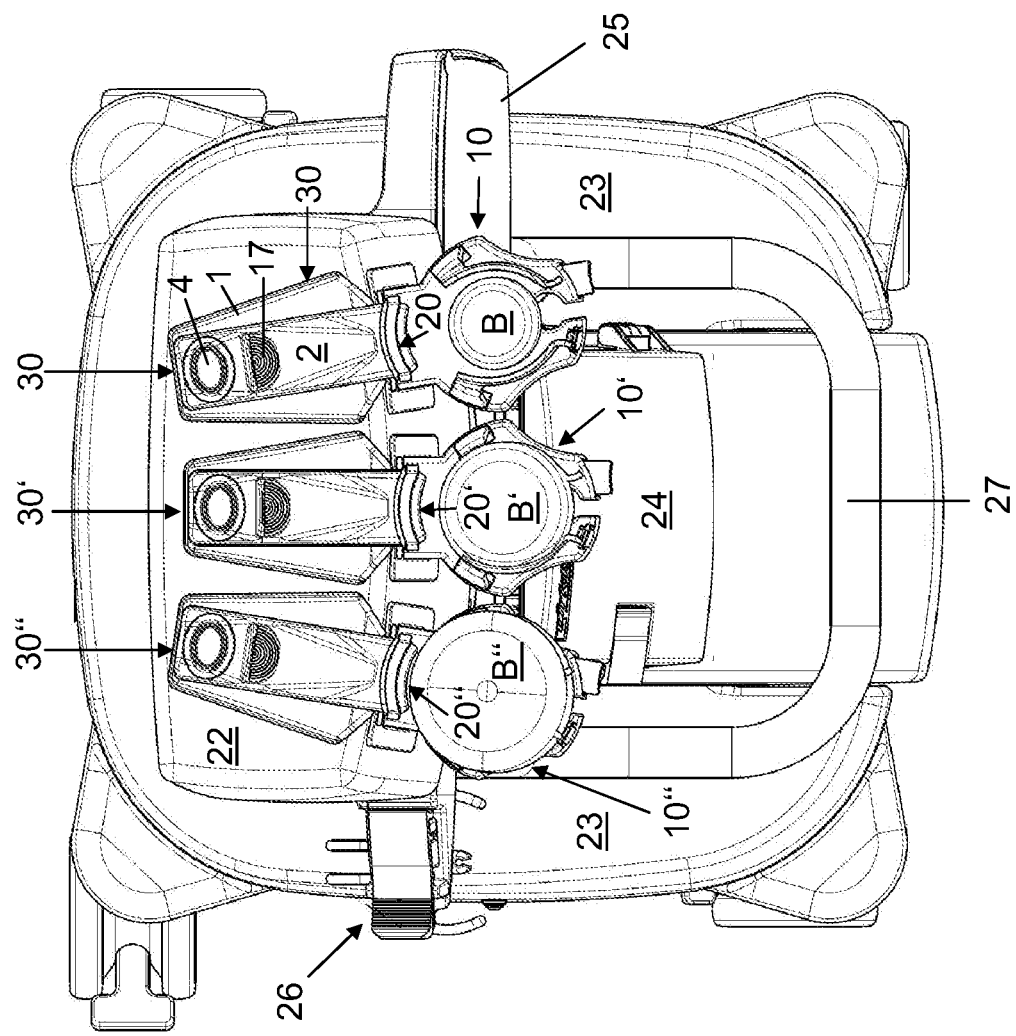
FIG. 3: a top view of the injector shown in FIG. 1.

FIGS. 1-3 show an injector for injecting contrast media into the human or animal body. The injector I comprises a frame structure with a foot part 23 mounted on rollers, a head part 22 and a shaft part 21 which connects the foot part 23 and the head part 22 to one another. In the head part 22, the injector I comprises a container holder according to the disclosure, which in the practical example illustrated comprises three container clamping members 10, 10', 10" for clamping on containers B, B', B". Each of the containers B, B', B" is filled with a contrast medium or with a rinsing solution (for example, a NaCl solution). The containers B, B', B" are exchangeably clamped onto the container clamping members 10, 10', 10." The containers (which hereinafter will be uniformly referred to as B) are, for example, bottles of different shapes and sizes, which have a bottleneck and which are clamped upside down (i.e., with the bottleneck oriented downwardly) onto the associated container clamping member 10, 10', 10" where they are held.

Disposed on the shaft part 21 is a pumping unit 24 with a peristaltic pump. In addition, a monitor 25 and a connecting device 26 are attached to the shaft part 21. The pumping unit 24 serves to deliver the fluids contained in the containers B into a patient's tube. To this end, a patient's tube (not shown) in the drawings is connected to a pump tube (also not shown in the drawings) to the connecting device 26. The pump tube is connected to the containers B by means of a tubular system or by means of a cartridge comprising fluid channels disposed therein via a branching section and connecting tubes disposed thereon. It is also possible to design the patient's tube and the pump tube as a single tube section and to connect this tube section directly to a cartridge. To deliver the fluids from the containers B into the patient's tube, the pump tube is placed into the peristaltic pump of the pumping unit 24. The containers B, which can each have a different shape and size, are filled with different contrast media or with a rinsing solution, and via the tubular system or the cartridge, it is possible to determine by opening or closing valves, from which container B the fluid contained therein is removed and pumped by means of the pumping unit 24 into the patient's tube.

As FIG. 3 indicates, a temperature control device 20, 20', 20" is dedicated to and disposed on each container clamping member 10, 10', 10". The temperature control devices 20, 20', 20" serve to control the temperature of the containers B, B', B" that are clamped onto the container clamping members 10, 10', 10". Each temperature control device 20, 20', 20" is connected to an associated transporting device 30, 30', 30". The transporting devices 30, 30', 30" serve to transport the temperature control devices 20, 20', 20" to the containers B, B', B" which are clamped onto the container clamping members 10, 10', 10".

Figure 4:
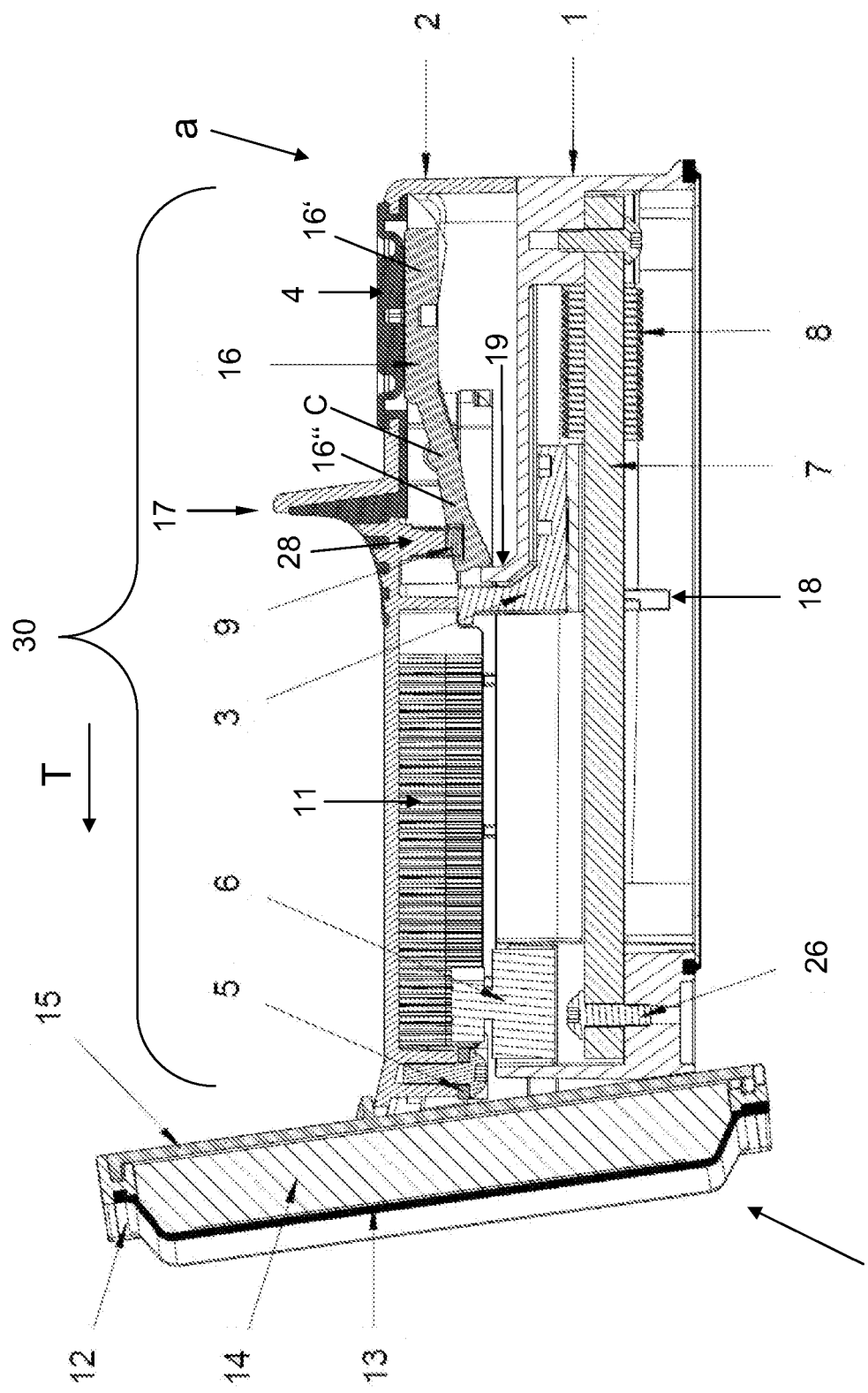
FIG. 4: a sectional view of a temperature control device and a connected transporting device of the injector shown in FIGS. 1-3 in a rearward position.
Figure 5:
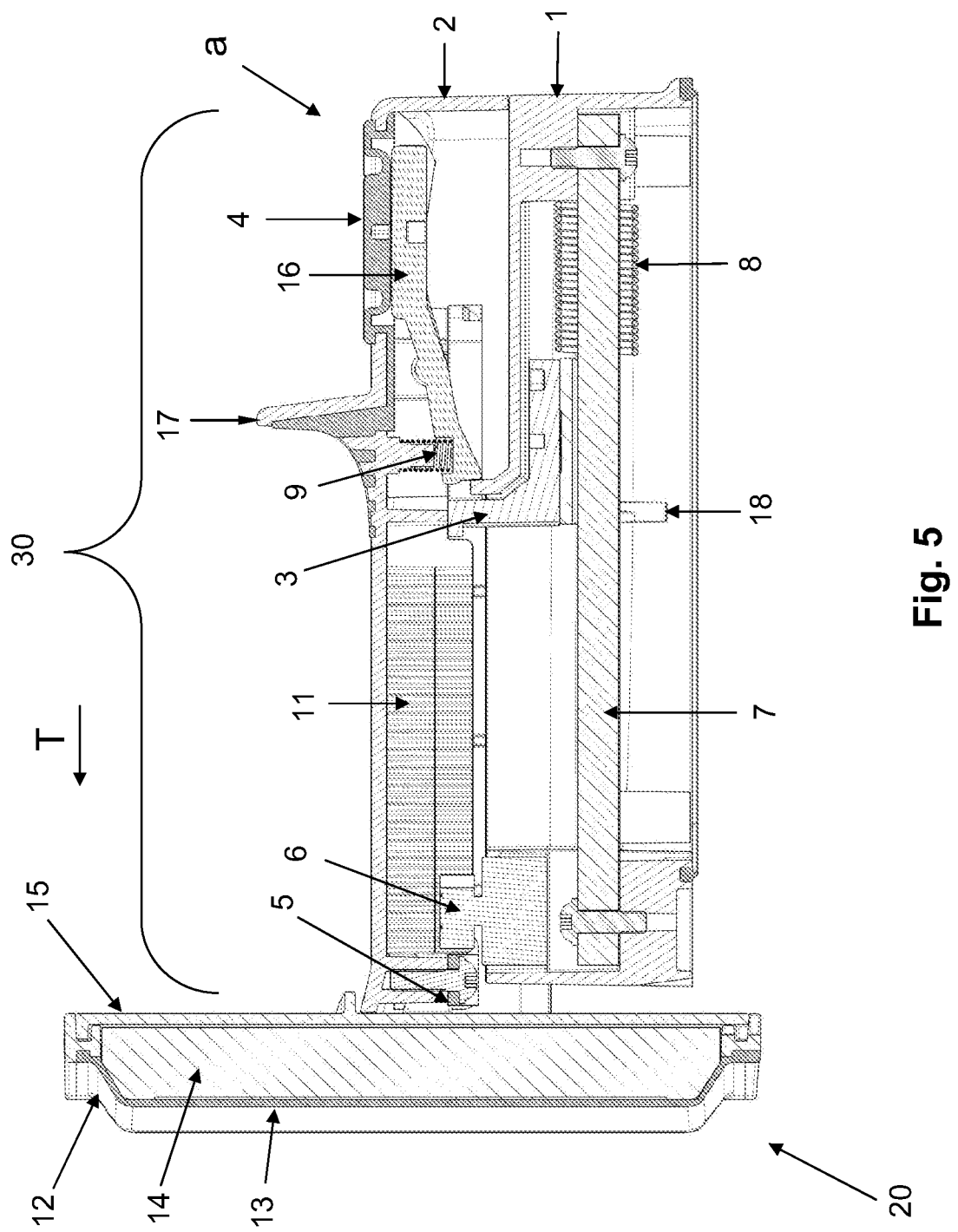
FIG. 5: a sectional view of the temperature control device and the connected transporting device shown in FIG. 4 in the rearward position, wherein the temperature control device is shown in a position that is pivoted with respect to the position shown in FIG. 4.
Figure 6:
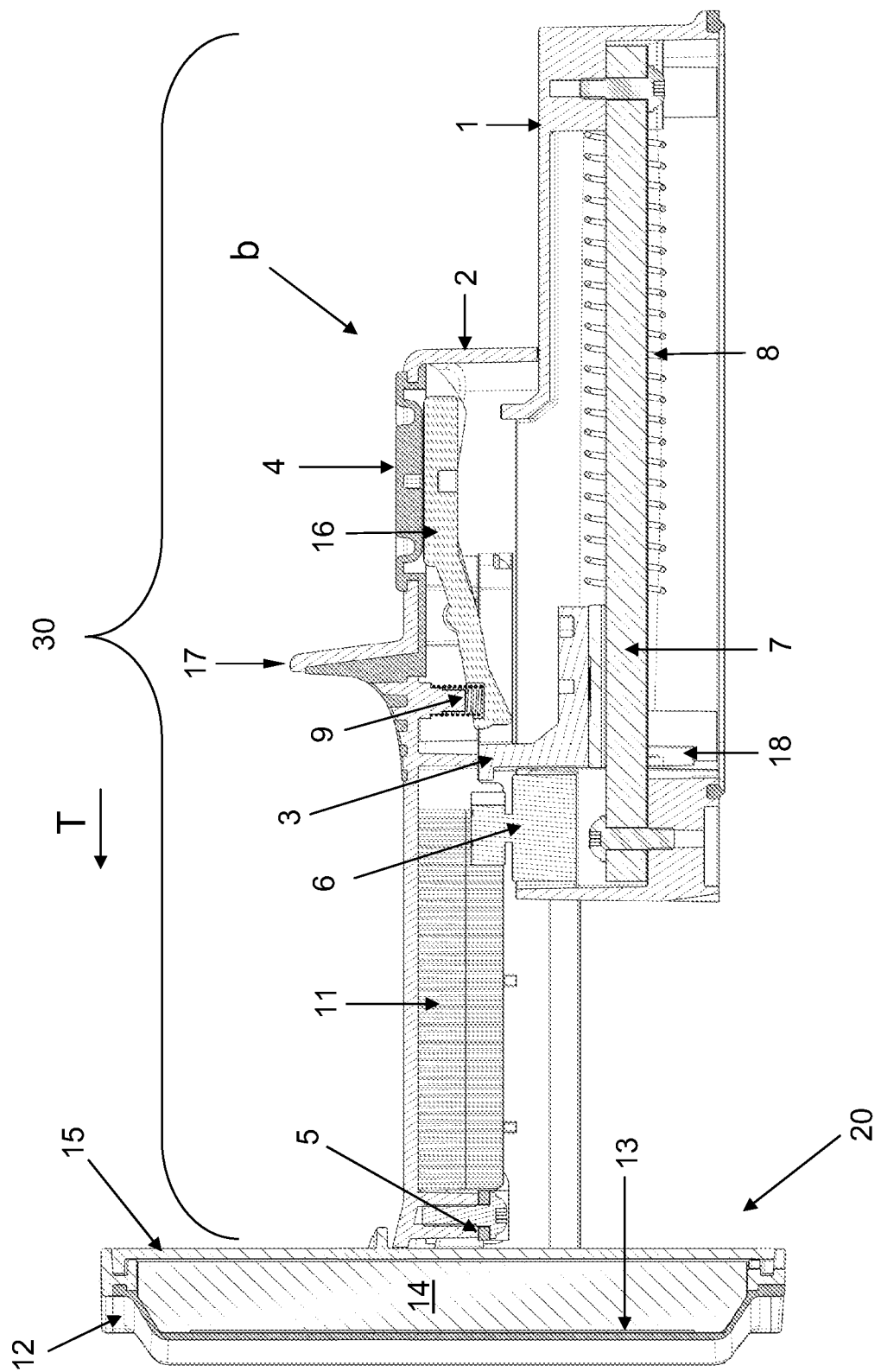
FIG. 6: a sectional view of the temperature control device and the connected transporting device shown in FIG. 4 in a forward position.

By way of an example, FIGS. 4-6 show longitudinal sections through a temperature control device 20 with a transporting device 30 connected thereto.

As FIG. 3 shows, the cross section of the temperature control device 20 has a curved or, more specifically, a concavely curved shape, in particular a part-cylindrical shape, for example, the shape of half of a cylinder, the shape of a third of a cylinder or the shape of a quarter of a cylinder. The temperature control device 20 comprises a heat-conducting element 12, a cooling or heating element 13 disposed thereon, a thermal insulator 14, which is made of an elastically deformable and non-heat conducting material, and a base member 15 disposed on the thermal insulator 14. The heat-conducting element 12 is configured, for example, as a multi-component plastic injection molded part, and comprises a main body made of a rigid plastic and an elastic layer made of an elastomer, with the elastomer layer facing the cooling or heating element 13 and being thermally conductively connected to said cooling or heating element.

Connected to the temperature control device 20 is a transporting device 30. The transporting device 30 comprises a housing 1, which is attached to the injector I, and a lid-shaped carriage 2 which, relative to the housing 1, moves linearly along a direction of movement T. The carriage 2 is mounted on a guide member 7, which is connected to the housing, so as to be able to move against the elastic force of a spring 8. To this end, a connector part 3 is attached to the carriage 2, and the connector part 3 is spring-mounted on the guide member 7 and is able to move along the guide member 7. Disposed on the lower surface of the connector part 3 is a projecting pin 18 which projects downwardly beyond the guide member 7.

Disposed on the inside surface of the lid-shaped carriage 2 is a gear rack 11 which meshes with a gear wheel of a damping element 6 designed in the form of a rotational damper. The damping element 6 is mounted on the housing 1. This allows the damping element 6 to dampen a translatory movement of the carriage 2 relative to the housing 1.

The carriage 2 moves relative to the housing 1 between a rearward position a, which is shown in FIGS. 4 and 5, and a forward position b, which is shown in FIG. 6. In the rearward position a, the temperature control device 20, which is connected to the transporting device 30, is positioned at a distance from a container B that is clamped onto a bottle clamping member 10 (not shown in FIGS. 4 to 6). In the forward position b, the temperature control device 20 is in thermal contact with the container B that is clamped onto the bottle clamping member 10.

To secure the carriage 2 in its rearward position a, a locking mechanism is provided. The locking mechanism comprises a swivel lever 16 which swivels about axis C, which is located in a direction vertical to the direction of movement T, and a detent 19 which is molded onto the housing 1. The swivel lever 16 comprises a rearward wing 16' and a forward wing 16", with the forward wing 16" having a groove, into which a pin 30 that is molded onto the carriage 2 engages, which pin has a pressure spring 9 disposed on the lower end of the pin 30. The swivel lever 16 can be swiveled about axis C by exerting pressure on the rear wing 16' of the swivel lever 16. To allow actuation of the swivel lever 16, a rearward wing 16' of the swivel lever is connected to a push button 4 made of an elastic material, for example, an elastomer or a rubber material. The push button 4 is located in an opening in the upper wall of the carriage 2 and is in mechanical contact with the rear wing 16' of the swivel lever 16. When (manual) pressure is exerted on the push button 4, the push button 4 is pushed downwardly into the inside of the carriage 2 and thereby exerts pressure on the rear wing 16' of the swivel lever 16, which causes the swivel lever to swivel about axis C against the elastic force of the pressure spring 9. As the swivel lever 16 is being swiveled, the forward edge of the front wing 16" of the swivel lever 16 is disengaged from the detent 19. This releases the locking mechanism which secures the carriage 2 in its rearward position a, and the carriage 2 is linearly moved by the elastic force of the spring 8 in the direction of movement T forwardly into a forward position b. When a container B is clamped onto the container clamping member 10 dedicated to the temperature control device 20, the carriage 2 is pushed forward by the spring 8 until the heat-conducting element 12, which forms a heat transfer zone, comes into contact with the outside surface of the container B that is clamped onto the container clamping member 10. This forward position b is shown in FIG. 6. Moving the carriage 2 into its forward position b causes the temperature control device 20 to be brought into thermal contact with the container B.

A handle part 17 is molded onto the upper surface of the carriage 2. The handle part 17 serves to manually move the carriage 2 back into its rearward position a. To move the carriage 2 back into its rearward position a, grasping the handle part 17 and exerting a pushing or pulling force oriented in a direction opposite to the direction of movement T and against the elastic force of the spring 8 allows the carriage 2 to be manually moved back until the carriage 2 reaches its rearward position a. After reaching the rearward position a, the locking mechanism catches since the forward locking edge of the forward wing 16" of the swivel lever 16 engages the detent 19 of the housing 1 as shown in FIGS. 4 and 5.

It is also possible to provide a motor drive for moving the carriage 2 back into its rearward position a. In that case, the handle part 17 can be omitted.

A sensor (not shown in the drawings) for detecting the position of the transporting device 30 is preferably provided. The sensor for detecting the position of the transporting device 30 can be configured, for example, as an optical sensor which detects the position of the pin 18 disposed on the lower surface of the connector part 3. However, the sensor for detecting the position of the transporting device 30 can also be a position switch, for example, a touch-sensitive limit switch or an inductive or capacitive position sensor. The sensor for detecting the position of the transporting device 30 is connected to a control unit which supplies the temperature control device 20 with the electrical current required for operating the cooling or heating element 13. The control unit is designed so that the current supply to the cooling or heating element 13 is cut off as soon as the carriage 2 is located in its rearward position a. As soon as the carriage 2 leaves its rearward position a and arrives in a forward position b, the control unit switches on the current supply to the cooling or heating element 13 in order to activate the temperature control device 20 for heating or cooling a container B that is clamped onto the container clamping member 10.

The container clamping member 10 preferably comprises a temperature sensor for detecting the temperature of a container B that is clamped onto the container clamping member 10. The temperature sensor is connected to the control unit as well and transmits the detected temperature of the container B to the control unit which controls the current supply to the cooling or heating element 13 as a function of the temperature detected by the temperature sensor, in such a way that the temperature of the container B is brought to a predefined target temperature and is maintained at this target temperature during an injection procedure.

As a comparison of FIGS. 4 and 5 shows, the temperature control device 20 can be swiveled relative to a vertical plane. To this end, the temperature control device 20 is pivotably mounted to the carriage 2 by means of a hinge 5 so as to pivot about an axis that is vertical relative to the direction of movement T. The hinge 5 allows the temperature control device 20 to swivel about the vertical baseline position of the temperature control device 20 as shown in FIG. 5, preferably within a limited angular range, for example, from ±5° to ±20°.

According to a useful embodiment of the disclosure, the housing 1 of the transporting device 30 is made of a transparent or translucent plastic material, and inside the housing 1, a light source, for example, an LED, is disposed. The light source is controlled by the control unit and indicates the operating statuses of the injector I and/or the temperature control device. Thus, based on different emitting colors of the light source, it is possible to determine, for example, whether a container B is clamped onto a container clamping member 10 that is dedicated to the temperature control device 20 and the associated transporting device 30 and/or whether the temperature control device 20 is activated. An additional light source, in particular in the form of an LED, can also be disposed on the temperature control device 20, for example, on the base member 15 or on the cooling or heating element 13, so as to indicate operating statuses of the temperature control device 20.

The invention claimed is:

1. A container holder for an injector for injecting a fluid into the human or animal body, the container holder comprising a container clamping member for clamping onto a container filled with the fluid and a temperature control device for heating or cooling the container to a predefined temperature, wherein the temperature control device is connected to a transporting device such that the temperature control device is moveable into and out of contact with the container which is clamped into the container clamping member.

2. The container holder of claim 1, wherein the temperature control device comprises an adjustable heating element or cooling element.

3. The container holder of claim 2, further comprising a sensor for detecting at least one of a position of the temperature control device and the transporting device.

4. The container holder of claim 3, wherein the sensor and the temperature control device are connected to a control unit which supplies the temperature control device with electrical current for operating the cooling or heating element as soon as the temperature control device reaches or leaves a predefined position.

5. The container holder of claim 1, wherein the temperature control device comprises a heat-conducting element which sits close to an outside surface of the container when the temperature control device is in thermal contact with the container that is clamped into the container clamping member.

6. The container holder of claim 1, wherein the temperature control device is moveable by the transporting device between a rearward position and at least one forward position, with the temperature control device being located at a distance from the container that is clamped into the container clamping member, when in the rearward position, and in thermal contact with the container when in the at least one forward position.

7. The container holder of claim 6, wherein a locking mechanism secures the transporting device in at least one of the rearward position and in the at least one forward position.

8. The container holder of claim 7, wherein the locking mechanism comprises a manually operable push button which, when activated, disengages the locked transporting device in at least one of the rearward position and the at least one forward position.

9. The container holder of claim 1, wherein the transporting device comprises a housing, which is securable to the injector, and a carriage which is moveable relative to the housing.

10. The container holder of claim 9, wherein the carriage is spring-mounted in or on the housing.

11. The container holder of claim 9, wherein the carriage is movably mounted on a guide member.

12. The container holder of claim 9, wherein a handle part is molded onto the carriage, by means of which handle part the movable carriage is manually moveable from a forward position, in which the temperature control device is in thermal contact with the container, into a rearward position, in which the temperature control device is located at a distance from the container.

13. The container holder of claim 1, wherein the temperature control device comprises a base member which is pivotably articulated on a front face of the transporting device.

14. The container holder of claim 13, wherein the transporting device comprises a damping element which dampens the movement of the carriage.

15. The container holder of claim 14, wherein the carriage comprises a gear rack which is connected to the damping element which is configured as a rotational damper.

16. The container holder of claim 13, wherein on the base element of the temperature control device, a cooling or heating element is disposed and wherein a thermal insulator is disposed between the base element and the cooling or heating element.

17. The container holder of claim 16, wherein the thermal insulator is made of an elastically deformable material.

18. The container holder of claim 1, wherein the transporting device comprises a spring and wherein the temperature control device is moved by an elastic force of the spring in a direction of a container that is clamped into the container clamping member so as to bring the temperature control device into thermal contact with the container.

\* \* \* \* \*